United States Patent
Katz et al.

(10) Patent No.: US 10,441,188 B2
(45) Date of Patent: Oct. 15, 2019

(54) AUTOMATIC DISPLAY OF EARLIEST LAT POINT

(71) Applicant: BIOSENSE WEBSTER (ISRAEL) LTD., Yokneam (IL)

(72) Inventors: Natan Sharon Katz, Atlit (IL); Benjamin Cohen, Haifa (IL); Lior Zar, Poria Illit (IL); Dror Berman, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 144 days.

(21) Appl. No.: 15/702,340

(22) Filed: Sep. 12, 2017

(65) Prior Publication Data
US 2019/0076045 A1    Mar. 14, 2019

(51) Int. Cl.
| | | |
|---|---|---|
| A61B 5/042 | (2006.01) | |
| A61B 5/00 | (2006.01) | |
| A61B 5/06 | (2006.01) | |
| G16H 50/50 | (2018.01) | |
| A61B 5/04 | (2006.01) | |
| A61B 5/044 | (2006.01) | |
| A61B 17/00 | (2006.01) | |

(52) U.S. Cl.
CPC ............ *A61B 5/0422* (2013.01); *A61B 5/044* (2013.01); *A61B 5/04012* (2013.01); *A61B 5/061* (2013.01); *A61B 5/6852* (2013.01); *A61B 5/6858* (2013.01); *G16H 50/50* (2018.01); *A61B 2017/00053* (2013.01)

(58) Field of Classification Search
CPC ... A61B 5/04012; A61B 5/0422; A61B 5/044; A61B 5/061; A61B 5/6852; A61B 5/6858; A61B 2017/00053; G16H 50/50

USPC .......................................................... 600/509
See application file for complete search history.

(56) References Cited

U.S. PATENT DOCUMENTS

| | | | |
|---|---|---|---|
| 5,738,096 A | 4/1998 | Ben-Haim | |
| 6,226,542 B1 * | 5/2001 | Reisfeld | A61B 5/04011 600/407 |
| 6,236,883 B1 * | 5/2001 | Ciaccio | A61B 5/04525 600/515 |
| 6,301,496 B1 * | 10/2001 | Reisfeld | A61B 5/04011 345/419 |
| 6,814,733 B2 | 11/2004 | Yitzhack Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |

(Continued)

OTHER PUBLICATIONS

European Search Report dated Jan. 29, 2019 from corresponding European Patent Application No. 18193757.4.

(Continued)

*Primary Examiner* — Christopher A Flory
(74) *Attorney, Agent, or Firm* — Vincent J. Serrao (57) ABSTRACT

Cardiac catheterization is carried out by inserting a multi-electrode probe into a heart of a living subject, preparing a current position map of the electrodes to define respective locations of the electrodes, and recording electrograms from the electrodes. Activation times are annotated at the respective locations by analysis of the electrograms and generating an activation map. A region of the activation map is selected and earliest ones of the activation times in the selected region identified. The earliest activation times are graphically indicated.

14 Claims, 4 Drawing Sheets

(56) References Cited

U.S. PATENT DOCUMENTS

| | | | |
|---|---|---|---|
| 7,536,218 B2 | 5/2009 | Govari et al. | |
| 7,756,576 B2 | 7/2010 | Levin | |
| 8,478,383 B2 | 7/2013 | Bar-Tal et al. | |
| 9,101,333 B2 | 8/2015 | Schwartz | |
| 9,554,718 B2 | 1/2017 | Bar-Tal et al. | |
| 9,629,567 B2 | 4/2017 | Porath et al. | |
| 9,706,937 B2 | 7/2017 | Yellin | |
| 2002/0010392 A1* | 1/2002 | Desai | A61B 5/0422 600/374 |
| 2003/0036696 A1* | 2/2003 | Willis | A61B 5/0422 600/424 |
| 2005/0209524 A1* | 9/2005 | Donaldson | A61B 5/042 600/510 |
| 2006/0173251 A1 | 8/2006 | Govari et al. | |
| 2007/0038078 A1 | 2/2007 | Osadchy | |
| 2007/0197929 A1 | 8/2007 | Porath et al. | |
| 2009/0069704 A1* | 3/2009 | MacAdam | A61B 5/044 600/523 |
| 2009/0124915 A1* | 5/2009 | MacAdam | A61B 5/044 600/523 |
| 2011/0206256 A1* | 8/2011 | Ramanathan | A61B 5/04021 382/128 |
| 2014/0005563 A1* | 1/2014 | Ramanathan | A61B 5/04012 600/523 |
| 2014/0213922 A1* | 7/2014 | Narayan | A61B 5/0422 600/515 |
| 2014/0243641 A1* | 8/2014 | Boveja | A61B 6/463 600/374 |
| 2014/0343442 A1* | 11/2014 | Thakur | A61B 5/04525 600/509 |
| 2015/0073246 A1* | 3/2015 | Chmiel | A61B 18/1492 600/374 |
| 2015/0250399 A1* | 9/2015 | Laughner | A61B 5/0422 600/374 |
| 2016/0089050 A1* | 3/2016 | Thakur | A61B 5/04525 600/509 |
| 2016/0095530 A1* | 4/2016 | Dubois | A61B 5/0044 600/512 |
| 2016/0310030 A1* | 10/2016 | Yellin | A61B 5/0452 |
| 2017/0202470 A1* | 7/2017 | Urman | A61B 5/0472 |
| 2017/0202472 A1* | 7/2017 | Zeidan | A61B 5/0422 |
| 2017/0202515 A1* | 7/2017 | Zrihem | A61B 5/04525 |
| 2017/0221254 A1 | 8/2017 | Zar et al. | |
| 2017/0245774 A1* | 8/2017 | Narayan | A61B 5/042 |
| 2017/0246461 A1* | 8/2017 | Ghosh | A61B 5/4836 |
| 2017/0251942 A1* | 9/2017 | Brodnick | A61B 5/7221 |
| 2018/0160978 A1 | 6/2018 | Cohen et al. | |

OTHER PUBLICATIONS

Sakamoto, S. I. et al., "Vagal Denervation and Reinnervation After Ablation of Ganglionated Plexi", Journal of Thoracic and Cardiovascular Surgery, Mosby-Year Book, Inc. St. Louis, MO, US, vol. 139, No. 2, Feb. 1, 2010, pp. 444-452.

Wang, Yong et al., "Focal Atrial Tachycardia After Pulmonary Vein Isolation: Noninvasive Mapping with Electrocardiographic Imaging (ECGI)", Heart Rhythm, Elsevier, US, vol. 4, No. 8, Aug. 2, 2007, pp. 1081-1084.

Houben, Richard P.M. et al., "Automatic mapping of human atrial fibrillation by template matching", Heart Rhythm, Oct. 2006, pp. 1221-1228, vol. 3, No. 10.

Pending U.S. Appl. No. 15/086,220, filed Mar. 31, 2016.
Pending U.S. Appl. No. 15/375,358, filed Dec. 12, 2016.

* cited by examiner

AUTOMATIC DISPLAY OF EARLIEST LAT POINT

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to measurement of bioelectric currents. More particularly, this invention relates to systems for recording bioelectric signals from the heart using means inserted into the body.

The meanings of certain acronyms and abbreviations used herein are given in Table 1.

TABLE 1

Acronyms and Abbreviations

| | |
|---|---|
| ACL | Active Current Location |
| CFAE | Complex Fractionated Electrograms |
| CPM | Current Position Map |
| LAT | Local Activation Time |

2. Description of the Related Art

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated to restore the normal function of the heart insofar as is possible.

Mapping of the electrical activation time in the heart muscle requires that the location of the sensor within the heart be known at the time of each measurement. In the past, such mapping was performed using a single movable electrode sensor inside the heart, which sensor measured activation time relative to a fixed external reference electrode. This technique, however, requires calibration, for example impedance calibrations with adjustments for impedance unrelated to that of the body. Mapping of electrical activation time using a single electrode was, furthermore, a lengthy procedure, generally performed under fluoroscopic imaging, and thereby exposing the patient to undesirable ionizing radiation. Furthermore, in an arrhythmic heart, activation times at a single location may change between consecutive beats.

Because of the drawbacks of single-electrode mapping, a number of inventors have taught the use of multiple electrodes to measure electrical potentials simultaneously at different locations in the endocardium, thereby allowing activation time to be mapped more rapidly and conveniently, as described. Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

Regional analysis of electroanatomical maps of the heart has been employed to enhance diagnostic accuracy in the evaluation of conduction disturbances. For example, commonly assigned application Ser. No. 15/375,358, entitled Real Time Electroanatomical Coloring of the Heart, by Assaf Cohen et al., describes displaying the heart in first graphic image. Signals from catheter sensors are processed according to a predefined algorithm to generate respective outputs, A region on the first graphic image that is less than all of the first graphic image is selected according to locations of the sensors, and values derived from outputs of the sensors are displayed on the selected region as a second graphic image. Thereafter, the second graphic image is removed and replaced by an update.

SUMMARY OF THE INVENTION

At present, a physician looking for the origin of a focal arrhythmia performs a manual inspection of an electroanatomic map. Initially, in a selected map area, the physician manually finds a point with an earliest LAT value. Once the earliest LAT position has been found the physician can map in more detail around this point to isolate the actual earliest LAT region. The initial manual search for the earliest point is a "hit and miss" inspection, and is relatively time-consuming.

Embodiments of the invention allow a physician to select an area of the map where inspection for the earliest LAT value is to be performed. A processor performs an automatic inspection within the selected area (which could also be the whole map), and marks on the map the earliest LAT position or positions. The physician can then manually perform a second mapping around the marked point or points.

There is provided according to embodiments of the invention a method, which is carried out by inserting a multi-electrode probe into a heart of a living subject, preparing a current position map of the electrodes to define respective locations of the electrodes, recording electrograms from the electrodes, annotating activation times at the respective locations by analysis of the electrograms, generating an activation map of electrical propagation waves from the activation times, selecting a region of the activation map, identifying earliest ones of the activation times in the selected region, and graphically indicating the earliest ones of the activation times.

According to one aspect of the method, the region includes all of the activation map.

According to a further aspect of the method, generating an activation map includes modeling the heart as a simulated 3-dimensional surface.

According to yet another aspect of the method, the region is selected by a human operator.

According to still another aspect of the method, the region is selected automatically.

There is further provided according to embodiments of the invention an apparatus, including a multi-electrode probe adapted for insertion into a heart of a living subject, and a processor, which is configured to receive an electrical signal from the electrodes and to perform a method comprising: preparing a current position map of the electrodes to define respective locations of the electrodes, recording electrograms from the electrodes, annotating activation times at the respective locations by analysis of the electrograms, generating an activation map of electrical propagation waves from the activation times, in a selected region of the activation map automatically identifying earliest ones of the activation times in the selected region, and graphically indicating the earliest ones of the activation times.

There is further provided according to embodiments of the invention a computer software product including a non-transitory computer-readable storage medium in which computer program instructions are stored, which instructions, when executed by a computer, cause the computer to perform the steps of:

receiving electrical signals from a plurality of electrodes in a heart, preparing a current position map of the electrodes to define respective locations of the electrodes, recording electrograms from the electrodes, annotating activation times at the respective locations by analysis of the electrograms, generating an activation map of electrical propagation waves from the activation times, selecting a region of the activation map, automatically identifying earliest ones of the activation times in the selected region, and graphically indicating the earliest ones of the activation times.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
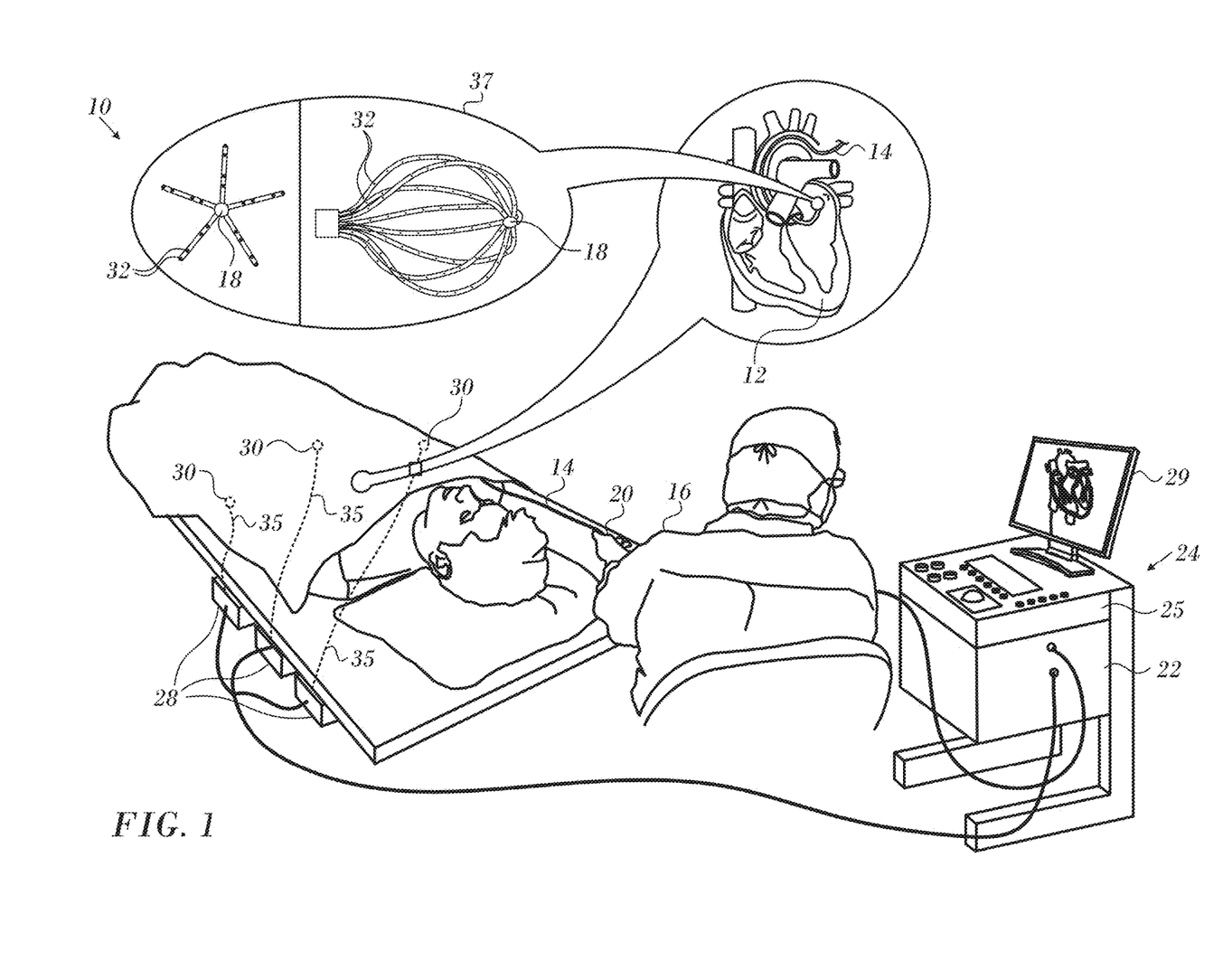
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765.

This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a balloon or basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

Figure 2:
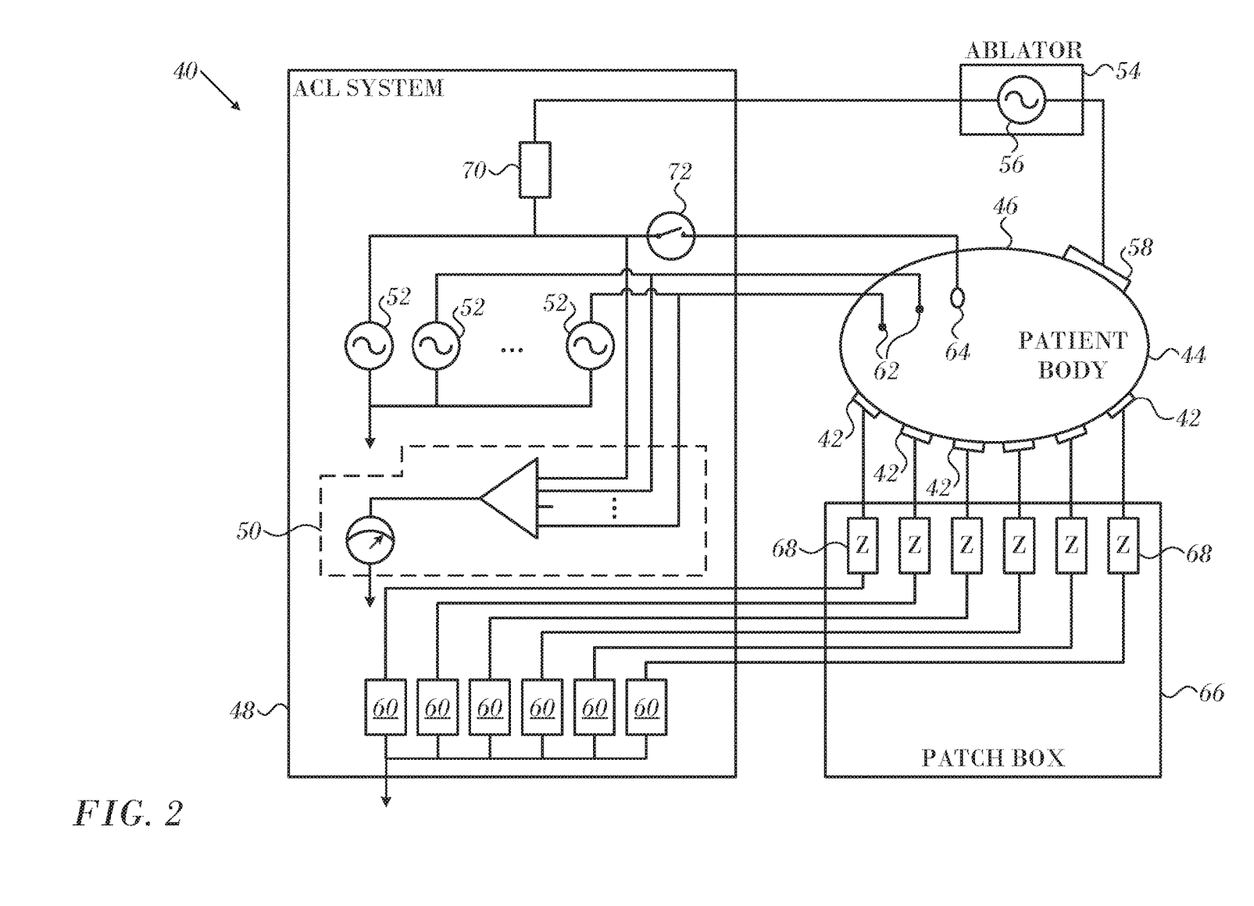
FIG. 2 is a schematic diagram of an ablation and active current location (ACL) circuit in accordance with an embodiment of the invention.

Reference is now made to FIG. 2, which is a schematic diagram of an ablation and active current location (ACL) circuit 40 for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 42, which can be adhesive skin patches, are coupled to a body surface 44 (e.g., the skin) of subject 46. The body surface electrodes 42 are sometimes referred to herein as "patches". In cardiac applications the body surface electrodes 42 are usually distributed so as to surround the heart, three on the chest of the subject and three on the back. However, the number of the body surface electrodes 42 is not critical, and they may be placed at convenient locations on the body surface 44 in the general vicinity of the site of the medical procedure.

A control unit 48, normally disposed in the console 24 (FIG. 1), includes current measurement circuitry 50 and one or more catheter electrode transmitters 52 for driving a current through one or more of the electrodes 42 to one or more of the body surface electrodes 42 at respective working frequencies. The control unit 48 is linked to a positioning processor (FIG. 1). The control unit 48 is linked to an ablator 54, which comprises at least one ablation generator 56. Currents through the body surface electrodes 42 and an ablator body surface electrode 58 flow in a circuit with the ablation generator 56 and are measured by respective current measurement circuits that are disposed within body electrode receivers 60, sometimes referred to herein as "patch measurement circuits". The body electrode receivers 60 are typically incorporated in the control unit 48. Alternatively, they may be affixed to the body surface electrodes 42. Catheter electrodes are represented as measurement electrodes 62 (circles) and a dual-purpose electrode 64 (ellipse). The dual-purpose electrode 64 functions as an ablation electrode and also serves as one of the measurement electrodes.

The body surface electrodes 42 are connected to the body electrode receivers 60 via a patch box 66, which protects the system from ablation and defibrillation currents. Typically the system is configured with six body electrode receivers 60. The patch box parasitic impedances 68 (Z), are measured during production and thus known a priori. These impedances are discussed below.

Typically, although only two measurement electrodes 62 are shown for convenience, about 80 measurement electrodes are used for impedance measurements. Typically there are one or two ablation electrodes. The coordinates of a catheter inside the body are determined in the positioning system by passing currents between electrodes on the catheter and the body surface electrodes 42.

The control unit 48 may also control an ablation circuit, comprising ablator 54, and the dual-purpose electrode 64. The ablator 54 is typically disposed externally to the control unit 48 and incorporates the ablation generator 56. It connects with the ablator body surface electrode 58 and to an ablator filter 70, which in this example is shown within the control unit 48. However this location is not essential. A switch 72 configures the ablator circuit for different modes of operation as described below. Voltage measurement circuitry is provided for determining the output of the catheter electrode transmitters 52. It will be noted from inspection that the ablation circuit is connected to one of the catheter electrode transmitters 52.

Figure 3:
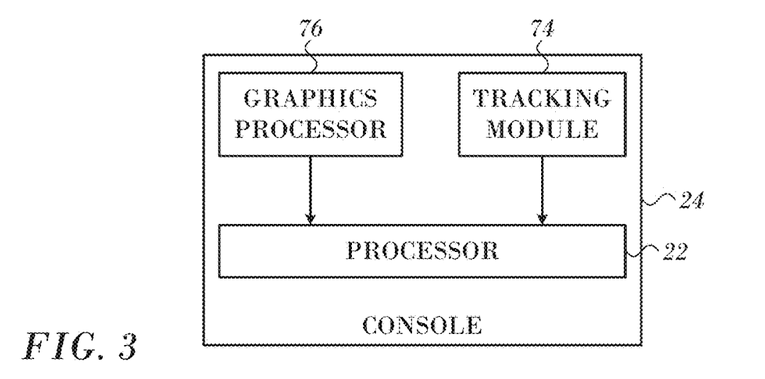
FIG. 3 is a block diagram of aspects of a processor of the system shown in FIG. 1 in accordance with an embodiment of the invention.

Reference is now made to FIG. 3, which is a block diagram of aspects of the processor 22 in accordance with an embodiment of the invention. Typically the processor 22 is located in the console 24 (FIG. 1), but it can be remote or distributed among several sites. The processor 22 may use a tracking module, such as tracking module 74, to convert signals from the above-noted location-sensing devices to location coordinates in a 3-dimensional frame of reference defined by the field generating coils 28 (FIG. 1). The processor 22 is linked to a graphics processor 76. The graphics processor 76 is a parallel processing unit that usually has approximately 2,000 processors. Functions of the graphics processor 76 are described below.

Figure 4:
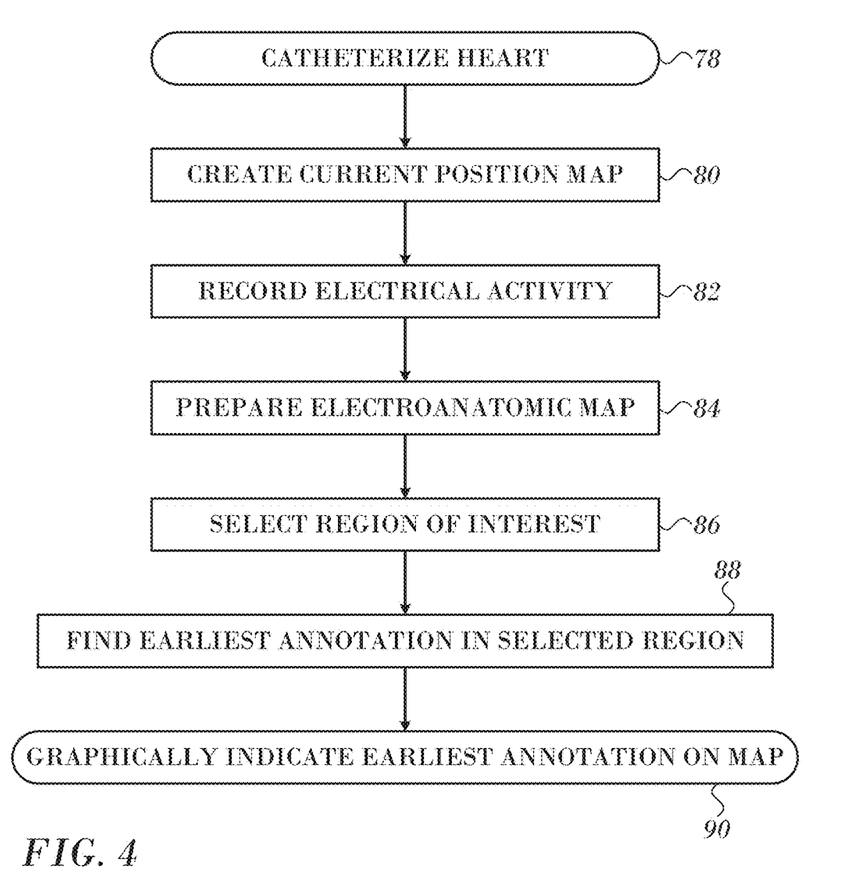
FIG. 4 is a flow chart of a method for identifying an earliest local activation time in electrical propagation through regions of the heart in accordance with an embodiment of the invention.

Reference is now made to FIG. 4, which is a flow chart of a method for identifying an earliest local activation time (LAT) in electrical propagation through regions of the heart in accordance with an embodiment of the invention. The process steps are shown in a particular linear sequence in FIG. 4 and the other flowcharts herein for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 78 the heart is catheterized conventionally with a multi-electrode mapping catheter. Catheters such as the PentaRay® NAV or Navistar® Thermocool® catheters, available from Biosense Webster, are suitable for initial step 78. The electrodes of the catheter are placed in galvanic contact with respective locations in one of the atria.

At step 80 the positions of the electrodes in the catheter are determined. One method of making the determination is the creation of a current position map (CPM). The CPM is generated using catheter 14 (FIG. 1), with an electrode (giving currents at a position) and a magnetic sensor (not shown) giving magnetic signals at the position together cooperatively with the ACL circuit 40 (FIG. 2).

Next, at step 82 atrial electrical activity is recorded concurrently with the multiple electrodes of the catheter, each now having a respective known location in a reference coordinate system. Depolarization is initially detected, where possible, using conventional methods such as the maximum −dV/dt deflection. The teachings of commonly assigned U.S. Pat. Nos. 9,101,333, 9,629,567, 9,554,718 and application Ser. No. 15/086,220 may be employed to more precisely identify and record atrial electrical activity, all of which are herein incorporated by reference. In the case of atrial LATS, ventricular far-field activity can be excluded using the methods taught in commonly assigned U.S. Pat. No. 9,706,937, which is herein incorporated by reference.

Next, at step 84 an annotated electroanatomic map is prepared, using the processor 22 (FIG. 3). Functional electroanatomic maps, e.g., electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. The above-noted CARTO 3 System is capable of generating such maps from catheter electrode readings.

Next, at step 86 a region of interest on the electroanatomic map prepared in step 84 is chosen. This may be done interactively with the operator 16 (FIG. 1). Alternatively, a region of interest may be chosen automatically based on analysis of the characteristics of the annotations, for example a region having an activation time interval of corresponding to a QRS complex in a body surface electrocardiogram, or regions having complex fractionated electrograms (CFAE), as explained in commonly assigned U.S. Patent Application Publication No. 2007/0197929 by Porath et al., which is herein incorporated by reference.

Listing 1

```
For each annotation in map
    If current annotation is in selected area   If LAT <= Earliest LAT then
        If LAT = Earliest LAT then
            add current annotation to
                set of earliest annotations
        else
            delete set of earliest annotations
            add current annotation to new set
                of earliest annotations
        end if
    end if
```

Next, at step 88 the processor 22 (FIG. 3) processor performs an automatic inspection within the selected area, (which could also be the entire map). The pseudocode in Listing 1 illustrates one way of identifying a set of earliest annotations.

Then at final step 90 the processor marks on the map each member of the set of earliest annotations. The set may have one or more members. The graphical indications of the set becomes immediately apparent to the operator 16, who may then navigate the catheter using the current position map developed in step 80 to perform a more detailed mapping in a smaller region that includes one or more members of the set of earliest annotations.

EXAMPLE

Figure 5:
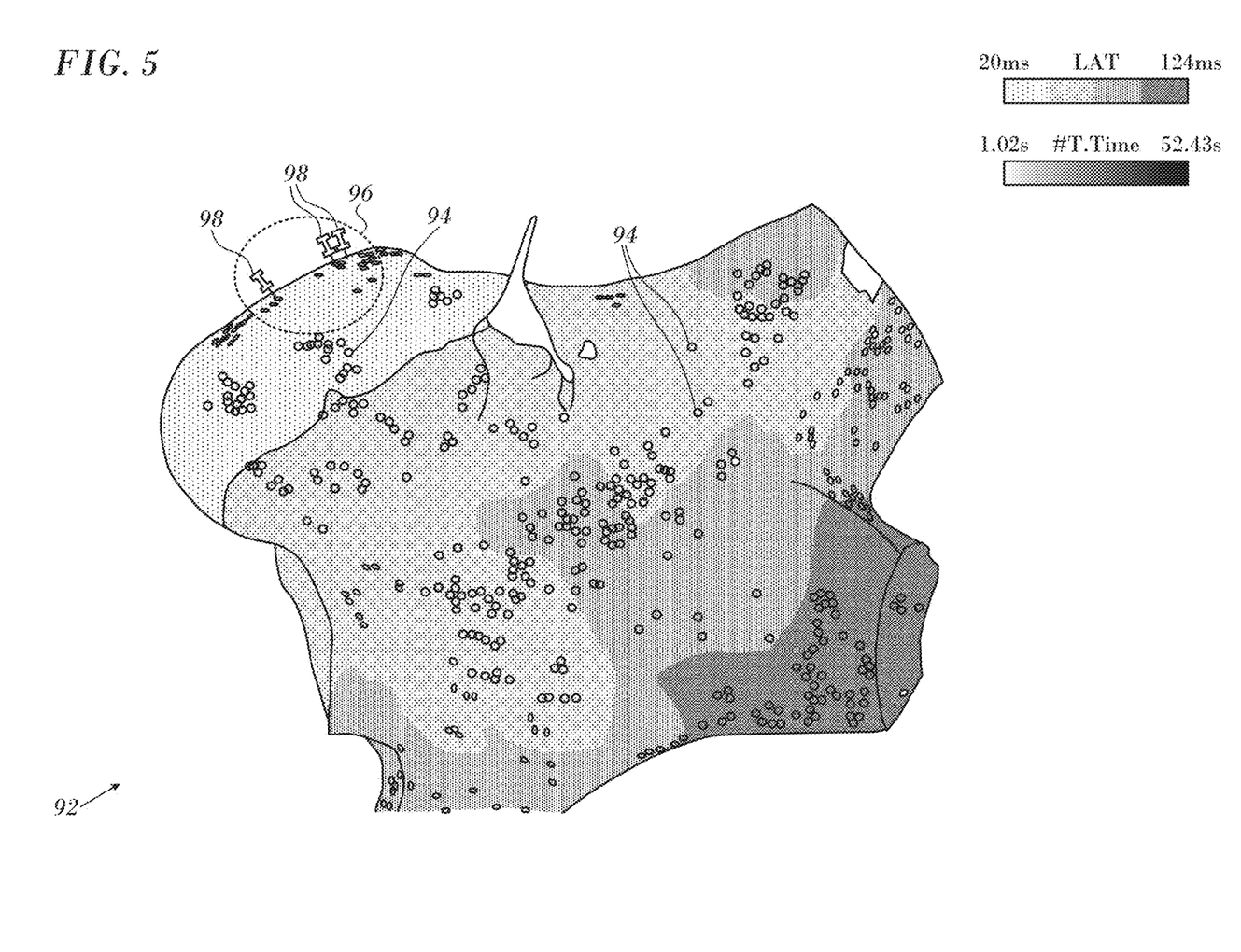
FIG. 5 is a simulated 3-dimensional image of a heart chamber in accordance with an embodiment of the invention.

Reference is now made to FIG. 5, which is a simulated 3-dimensional surface of a heart chamber 92 in accordance with an embodiment of the invention. Mapping was conducted according to the procedure described with respect to FIG. 4. Annotations are shown as small circles, indicated representatively by annotations 94. A region 96 was selected for automatic inspection, and a collection of three earliest annotations having the same LAT, which are graphically shown by indicators 98.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   inserting a probe into a heart of a living subject, the probe having a plurality of electrodes;
   receiving location signals from the electrodes indicative of the respective locations of the electrodes in a reference coordinate system;
   determining respective locations of the electrodes relative to the reference coordinate system using the location signals;
   receiving electrogram signals from the electrodes indicative of the electrical activity of the heart at the respective locations;
   annotating activation times at the respective locations by analysis of the electrogram signals;
   generating an activation map of electrical propagation waves from the activation times using a processor;
   selecting a region of the activation map;
   determining earliest LAT locations by the processor, comprising;
     automatically analyzing the activation map by identifying earliest ones of the activation times in the selected region; and
     graphically indicating the earliest ones of the activation times on the activation map.

2. The method according to claim 1, wherein the region comprises all of the activation map.

3. The method according to claim 1, wherein generating an activation map comprises modeling the heart as a simulated 3-dimensional surface.

4. The method according to claim 1, wherein the region is selected by a human operator.

5. The method according to claim 1, wherein the region is selected automatically.

6. The method according to claim 1 wherein determining respective locations of the electrodes comprises preparing a current position map of the electrodes.

7. An apparatus, comprising:
   a probe having a plurality of electrodes and adapted for insertion into a heart of a living subject; and
   a processor, which is configured to receive location signals from the electrodes indicative of the respective locations of the electrodes in a reference coordinate system and to perform the steps of:
     determining locations of the electrodes relative to the reference coordinate system using the location signals;
     receiving electrogram signals from the electrodes indicative of the electrical activity of the heart at the respective locations;
     annotating activation times at the respective locations by analysis of the electrogram signals;
     generating an activation map of electrical propagation waves from the activation times;
     in a selected region of the activation map automatically analyzing the activation map by identifying earliest ones of the activation times in the selected region; and
     graphically indicating the earliest ones of the activation times on the activation map.

8. The apparatus according to claim 7, wherein the region comprises all of the activation map.

9. The apparatus according to claim 7, wherein generating an activation map comprises modeling the heart as a simulated 3-dimensional surface.

10. A computer software product including a non-transitory computer-readable storage medium in which computer program instructions are stored, which instructions, when executed by a computer, cause the computer to perform the steps of:
    receiving location signals from a plurality of electrodes in a heart, the location signals indicative of the respective locations of the electrodes in a reference coordinate system;
    determining a current position map of the electrodes to define respective locations of the electrodes relative to the reference coordinate system using the location signals;
    receiving electrogram signals from the electrodes indicative of the electrical activity of the heart at the respective locations;
    annotating activation times at the respective locations by analysis of the electrogram signals;
    generating an activation map of electrical propagation waves from the activation times;
    selecting a region of the activation map;
    determining an earliest LAT locations by automatically identifying earliest ones of the activation times in the selected region; and
    graphically indicating the earliest ones of the activation times on the activation map.

11. The computer software product according to claim 10, wherein the region comprises all of the activation map.

12. The computer software product according to claim 10, wherein generating an activation map comprises modeling the heart as a simulated 3-dimensional surface.

13. The computer software product according to claim 10, wherein the region is selected by a human operator.

14. The computer software product according to claim 10, wherein the processor is instructed to select the region automatically.

* * * * *